United States Patent
Fan et al.

(10) Patent No.: US 11,529,219 B2
(45) Date of Patent: Dec. 20, 2022

(54) AUTOMATIC INTRAORAL 3D SCANNER USING LIGHT SHEET ACTIVE TRIANGULATION

(71) Applicant: CARESTREAM DENTAL TECHNOLOGY TOPCO LIMITED, London (GB)

(72) Inventors: Chuanmao Fan, San Jose, CA (US); Victor C. Wong, Pittsford, NY (US)

(73) Assignee: Dental Imaging Technologies Corporation, Quakertown, PA (US)

(*) Notice: Subject to any disclaimer, the term of this patent is extended or adjusted under 35 U.S.C. 154(b) by 371 days.

(21) Appl. No.: 16/626,977

(22) PCT Filed: Jun. 29, 2017

(86) PCT No.: PCT/US2017/039898
§ 371 (c)(1),
(2) Date: Dec. 27, 2019

(87) PCT Pub. No.: WO2019/005056
PCT Pub. Date: Jan. 3, 2019

(65) Prior Publication Data
US 2020/0138553 A1      May 7, 2020

(51) Int. Cl.
*A61C 9/00* (2006.01)
*A61C 7/08* (2006.01)

(52) U.S. Cl.
CPC ............ *A61C 9/006* (2013.01); *A61C 7/08* (2013.01); *A61C 9/0006* (2013.01)

(58) Field of Classification Search
CPC .......... A61C 9/006; A61C 9/0006; A61C 7/08
See application file for complete search history.

(56) References Cited

U.S. PATENT DOCUMENTS

| | | | | |
|---|---|---|---|---|
| 5,545,039 A * | 8/1996 | Mushabac | ............ | A61C 9/0053 433/218 |
| 5,857,853 A * | 1/1999 | van Nifterick | .... | A61C 13/0004 433/68 |
| 6,050,821 A * | 4/2000 | Klaassen | ............ | A61C 9/0086 433/214 |
| 6,364,660 B1 * | 4/2002 | Durbin | .................... | G06T 17/00 433/29 |
| 6,386,867 B1 * | 5/2002 | Durbin | .................... | A61C 9/00 433/25 |
| 7,494,338 B2 * | 2/2009 | Durbin | .................... | A61C 9/00 433/29 |

(Continued)

*Primary Examiner* — Nicholas D Lucchesi
(74) *Attorney, Agent, or Firm* — Alston & Bird LLC

(57) ABSTRACT

An intraoral scanning apparatus has a mouthpiece and a transport apparatus that defines at least a first curved track within the mouthpiece. An image sensor is movable along the first curved track. A scanner is movable along the first curved track, scanning in synchronization with the image sensor and having an illumination source that has a laser light source and beam-shaping optics in the path of the laser light for forming a linear light pattern. At least one actuator is energizable to move the image sensor and scanner along the first curved track for image acquisition. A control logic processor synchronizes the scanner and image sensor for automated acquisition of surface contour data. A display is in signal communication with the control logic processor to process and display the acquired surface contour data.

23 Claims, 14 Drawing Sheets

(56) References Cited

U.S. PATENT DOCUMENTS

| | | | |
|---|---|---|---|
| 7,599,538 B2* | 10/2009 | Crucs | A61B 6/145 |
| | | | 382/128 |
| 2002/0055082 A1* | 5/2002 | Durbin | A61C 9/00 |
| | | | 433/29 |
| 2004/0252312 A1* | 12/2004 | Chen | A61C 9/006 |
| | | | 356/603 |
| 2015/0140502 A1* | 5/2015 | Brawn | A61C 7/08 |
| | | | 433/29 |
| 2017/0080249 A1* | 3/2017 | Brawn | A61N 5/0603 |
| 2019/0083202 A1* | 3/2019 | Brawn | A61C 8/0006 |
| 2019/0282342 A1* | 9/2019 | Aubailly | A61B 1/045 |
| 2020/0138553 A1* | 5/2020 | Fan | A61C 7/08 |
| 2021/0085436 A1* | 3/2021 | Evans | A61C 17/0202 |

* cited by examiner

AUTOMATIC INTRAORAL 3D SCANNER USING LIGHT SHEET ACTIVE TRIANGULATION

TECHNICAL FIELD

The disclosure relates generally to intraoral diagnostic imaging and more particularly to an apparatus and method for intraoral scanning. More specifically, the disclosure relates to scanning apparatus and methods for characterizing intraoral surfaces without manual intervention.

BACKGROUND

Surface contour imaging uses patterned or structured light and triangulation to obtain surface contour information for an object. In contour imaging, a pattern of lines or other features is projected toward the surface of an object from a given angle. The projected pattern on the surface is then viewed from another angle as a contour image, taking advantage of triangulation in order to analyze surface information and to characterize the surface contour based on the deformed appearance of the projected lines. Phase shifting, in which the projected line pattern is incrementally spatially shifted for obtaining additional measurements at higher resolution, helps to more accurately map the object's surface.

Surface contour imaging using structured light has been employed for intraoral use and is acknowledged to be useful in a range of applications, including orthodontics and restorative dentistry. Proposed solutions for surface contour imaging have achieved some success, but there remains some room for improvement.

One particular challenge with dental surface imaging relates to tooth translucency. Translucent or semi-translucent materials in general are known to be particularly troublesome for patterned light imaging. Subsurface scattering in translucent structures can reduce the overall signal-to-noise (S/N) ratio and shift the light intensity, causing inaccurate height data. Another problem relates to specular reflection from tooth surfaces. Specular reflection can cause localized saturation in sensor response and can compromise accurate detection of structured light.

From an optical perspective, the structure of the tooth itself presents a number of additional challenges for structured light projection imaging. Teeth can be wet or dry at different times and along different surfaces and portions of surfaces. Tooth shape is often irregular, with sharp edges. As noted earlier, teeth interact with light in a complex manner. Light penetrating beneath the surface of the tooth tends to undergo significant scattering within the translucent tooth material. Moreover, reflection from opaque features beneath the tooth surface can also occur, adding noise that degrades the sensed signal and thus further complicates the task of tooth surface analysis. Not all light wavelengths can be detected with equal accuracy. Thus, a multi-spectral or multicolor approach can be less satisfactory in some cases.

Even where a coating or other type of surface conditioning of the tooth is used, however, results can be disappointing due to the pronounced contours of the tooth surface and inherent difficulties such as angular and space limitations. It can be difficult to provide sufficient amounts of light onto, and sense light reflected back from, all of the tooth surfaces. For example, different surfaces of the same tooth can be oriented at 90 degrees relative to each other, making it difficult to direct enough light for accurately imaging all parts of the tooth.

There have been a number of attempts to adapt structured light surface-profiling techniques to the problems of tooth structure imaging. For example, U.S. Pat. No. 5,372,502 entitled "Optical Probe and Method for the Three-Dimensional Surveying of Teeth" to Massen et al. describes the use of an LCD matrix to form patterns of stripes for projection onto the tooth surface. A similar approach is described in U.S. Patent Application Publication 2007/0086762 entitled "Front End for 3-D Imaging Camera" by O'Keefe et al. U.S. Pat. No. 7,312,924 entitled "Polarizing Multiplexer and Methods for IntraOral Scanning" to Trissel describes a method for profiling the tooth surface using triangularization and polarized light, but requiring application of a fluorescent coating for operation. Similarly, U.S. Pat. No. 6,885,464 entitled "3-D Camera for Recording Surface Structures, in Particular for Dental Purposes" to Pfeiffer et al. discloses a dental imaging apparatus using triangularization but also requiring the application of an opaque powder to the tooth surface for imaging. U.S. Pat. No. 6,885,464 to Pfeiffer et al. describes an intraoral camera that provides a group of light beams for imaging. Patent application WO 2011/145790 by Lim describes a 3-D scanner using scanned laser light. Patent application WO 2016/041147 by Liu describes a laser projection apparatus for contour imaging using a line laser.

Conventional methods for forming a pattern of lines of light include use of a 2-D array of micromirrors, such as those provided by a Digital Light Processor (DLP) from Texas Instruments, Inc., Dallas, Tex. Designs proposed for using these devices, however, are bulky and poorly suited for applications such as intraoral imaging. Alternate solutions using 2-D scanners have been proposed; however, these solutions do not allow imaging at the needed speed for intraoral applications.

An inherent problem with portable intraoral scanning devices relates to the small field of view (FOV) of imaging optics and scanning hardware. Since only a small portion of the scanned dental arch can be imaged at a time, obtaining a scan of the full dental arch, or of any substantial segment of the dental arch, requires that successive scan images be registered to each other so that scan data from the image sequence can be accurately stitched together to image a continuous scanned surface.

Data processed from the scanner is used to generate point cloud data that can be used to provide a 3D mesh that models the scanned surface contour. Point cloud generation is typically performed synchronously with scanning. Obtaining high resolution for point cloud generation requires careful, coordinated movement of the intraoral scan device, including device positioning and orientation that obtains image content from the scanned teeth and related features.

Thus, the task of performing a full intraoral scan using structured light imaging requires skill and takes time, typically on the order of 5-10 minutes with conventional intraoral scan devices. It can be appreciated that there would be significant benefits to optical scanning apparatus that automate the scanning process, with built-in registration and the capability for high-resolution scan acquisition.

SUMMARY

An object of the present disclosure is to address the need for accurate characterization of the surface contour of teeth and other intraoral structures. Certain exemplary method and/or apparatus embodiments employ techniques that can automate scanning and subsequent image capture so that full mouth imaging can be obtained without requiring extensive practitioner time and without highly sophisticated, stationary imaging systems.

These objects are given only by way of illustrative example, and such objects may be exemplary of one or more embodiments of the invention. Other desirable objectives and advantages inherently achieved by the may occur or become apparent to those skilled in the art. The invention is defined by the appended claims.

According to one aspect of the application, there is provided an intraoral scanning apparatus comprising:
 a) a mouthpiece;
 b) a transport apparatus that defines at least a first curved track within the mouthpiece;
 c) an image sensor movable along the first curved track;
 d) a scanner movable along the first curved track, scanning in synchronization with the image sensor and having an illumination source that has:
   (i) a laser light source;
   (ii) beam-shaping optics in the path of the laser light for forming a linear light pattern;
 e) at least one actuator energizable to move the image sensor and scanner along the first curved track for image acquisition;
 f) a control logic processor that synchronizes the scanner and image sensor for automated acquisition of surface contour data;
 and
 g) a display in signal communication with the control logic processor to process and display the acquired surface contour data.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DESCRIPTION OF EXEMPLARY EMBODIMENTS

Figure 1:
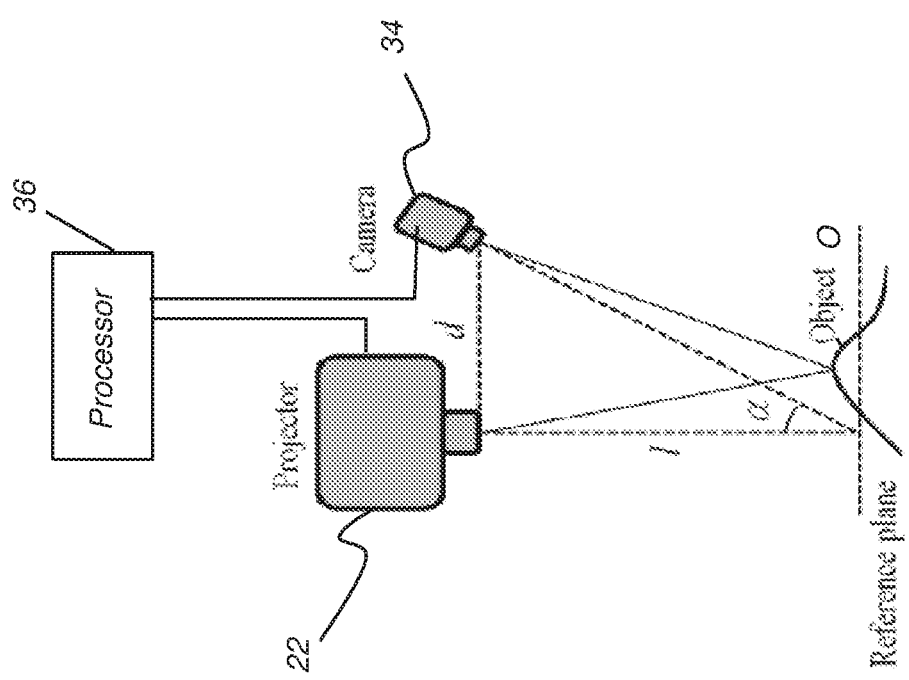
FIG. 1 is a schematic diagram that shows how triangularization is used to obtain surface contour data.

The following is a description of exemplary method and/or apparatus embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the term "optics" is used generally to refer to lenses and other refractive, diffractive, and reflective components or apertures used for shaping and orienting a light beam. An individual component of this type is termed an optic.

In the context of the present disclosure, the terms "viewer", "operator", and "user" are considered to be equivalent and refer to the viewing practitioner, technician, or other person who may operate a camera or scanner and may also view and manipulate an image, such as a dental image, on a display monitor. An "operator instruction" or "viewer instruction" is obtained from explicit commands entered by the viewer, such as by clicking a button on a camera or scanner or by using a computer mouse or by touch screen or keyboard entry. The term "subject" refers to the tooth or other portion of a patient that is being imaged and, in optical terms, can be considered equivalent to the "object" of the corresponding imaging system.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the term "camera" relates to a device that is enabled to acquire a reflectance, 2D digital image from reflected visible or NIR (near-infrared) light, such as structured light that is reflected from the surface of teeth and supporting structures.

In the context of the present disclosure, the term "structured light illumination" or "patterned illumination" are used to describe the type of projected illumination that is used for surface imaging or "contour" imaging that characterizes tooth shape. The structured light pattern itself can include, as patterned light features, one or more lines, circles, curves, or other geometric shapes that are distributed over the area that is illuminated and that have a predetermined spatial and temporal frequency. One exemplary type of structured light pattern that is widely used for contour imaging is a pattern of evenly spaced lines of light projected onto the surface of interest.

In the context of the present disclosure, the terms "structured light image" and "contour image" are considered to be equivalent and refer to the image that is captured during projection of the light pattern that is used for characterizing the tooth contour.

Two lines of light, portions of a line of light, or other features in a pattern of structured illumination can be considered to be substantially "dimensionally uniform" when their line width is the same over the length of the line to within no more than +/−15 percent. Dimensional uniformity of the pattern of structured illumination can be used to maintain a uniform spatial frequency.

In the context of the present disclosure, the descriptive phrase "mechanically coupled" is intended to indicate a mechanical association, connection, relation, or linking, between two or more components, such that the disposition of one component affects the spatial disposition of a component to which it is coupled. For mechanical coupling, two components need not be in direct contact, but can be linked through one or more intermediary components. The phrase "optically coupled" indicates that the corresponding optical components are suitably disposed to pass an optical signal between them.

The descriptive term "arcuate" generally indicates a path or shape having curvature that can be approximately arc-shaped.

Certain exemplary method and/or apparatus embodiments of the application can provide a depth-resolved volume imaging for obtaining signals that characterize the surfaces of teeth, gum tissue, and other intraoral features.

Figure 2:
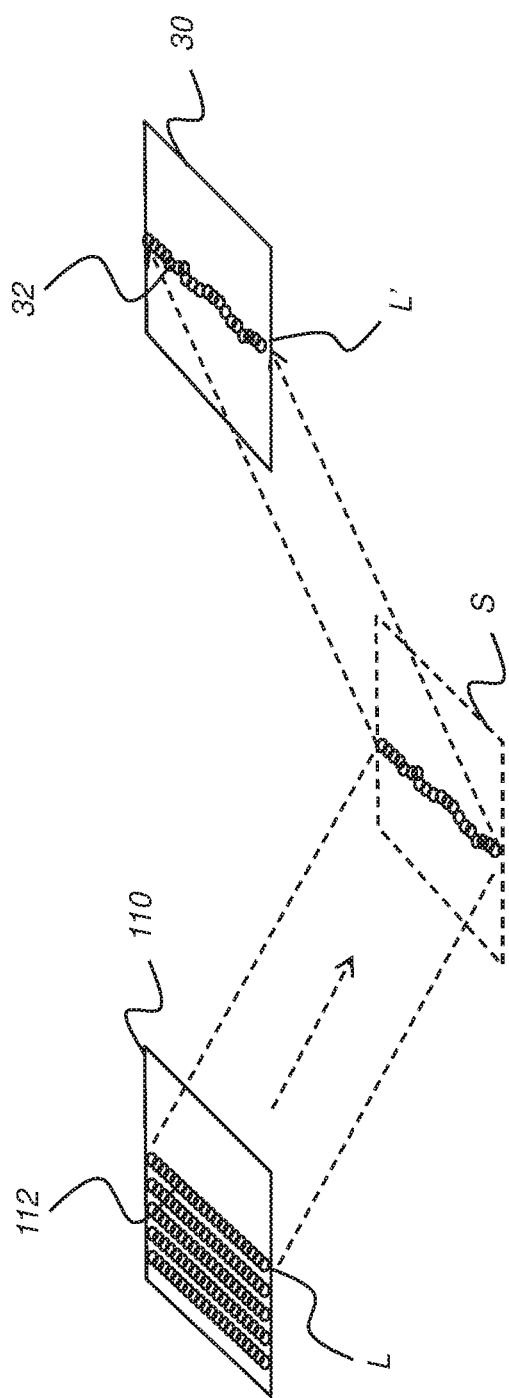
FIG. 2 is a schematic diagram that shows how patterned light is used for obtaining surface contour information.

The schematic diagrams of FIGS. 1 and 2 show how triangularization is used to obtain surface contour data of an object O. Provided by a scanning apparatus, a projector 22 and a camera or other type of image sensor 34 that includes appropriate imaging optics, separated by a distance d, cooperate to scan the surface contour. According to an exemplary embodiment of the present disclosure, projector 22 directs successive lines of illumination over a distance 1 onto the object O at a reference plane. Camera 34, acquires image content corresponding to each projected line. Principal axes of projector 22 and camera or image sensor 34 are offset from each other by an angle α. A control logic processor 36, such as a computer, dedicated microprocessor, or other logic processing device, synchronizes operation of projector 22 and camera or image sensor 34 and obtains, stores, and processes or transmits the acquired image data from camera 34 in order to characterize the surface contour of object O.

The schematic diagram of FIG. 2 shows, for the example of a single line of light L that is projected from an illumination array 110, how patterned light is used for obtaining surface contour information when using a conventional array source. A mapping is obtained as illumination array 110 directs a pattern of light from projector 22 onto a surface S and a corresponding image of a line L' is formed on an imaging sensor array 30 of camera 34. Each pixel 32 on imaging sensor array 30 maps to a corresponding pixel 112 on illumination array 110 according to modulation by surface S. Shifts in pixel position, as represented in FIG. 2, yield useful information about the contour of surface S. It can be appreciated that the basic pattern shown in FIG. 2 can be implemented in a number of ways, using a variety of illumination sources and sequences and using one or more different types of sensor arrays 30. Illumination array 110 can utilize any of a number of types of arrays used for light modulation, such as a liquid crystal array or digital micro-mirror array, such as that provided using the DLP device, as noted previously.

Using the concept described with reference to FIG. 2, conventional structured light imaging apparatus used for contour imaging, such as apparatus using digital light processor (DLP) and similar modulation systems, form and project a 2-D image, multiple lines at a time, onto the target surface. Certain exemplary embodiments of the present disclosure do not use an array for line generation, but instead use an alternate approach that directs a single line of light toward the subject at a time.

By projecting and capturing images that show structured light patterns that duplicate the illumination arrangement shown in FIG. 2 multiple times and at incremental intervals, the image of the contour line on the camera simultaneously locates a number of surface points of the imaged object. This speeds the process of gathering many sample points, while the plane of light (and usually also the receiving camera) is laterally moved in order to "paint" some or all of the exterior surface of the object with the plane of light.

Multiple structured light patterns can be projected and analyzed together for a number of reasons, including to increase the density of lines for additional reconstructed points and to detect and/or correct incompatible line sequences. Use of multiple structured light patterns is described in commonly assigned U.S. Patent Application Publications No. US2013/0120532 and No. US2013/0120533, both entitled "3D INTRAORAL MEASUREMENTS USING OPTICAL MULTILINE METHOD" and incorporated herein in their entirety.

Figure 3:
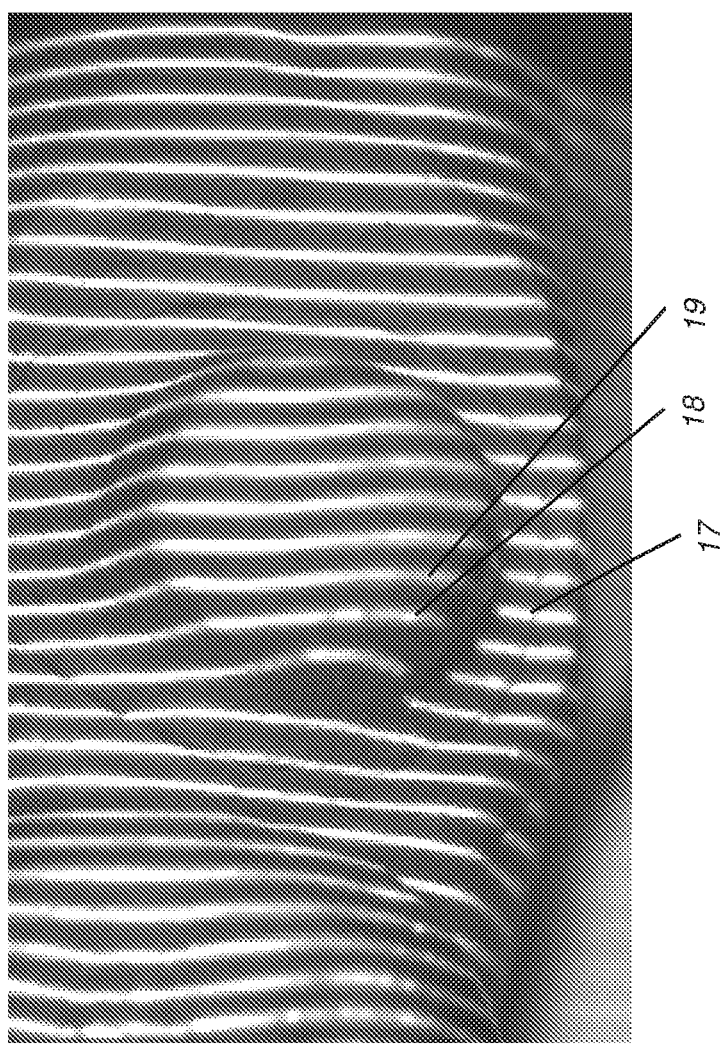
FIG. 3 is a diagram that shows surface imaging using a pattern with multiple lines of light.

FIG. 3 shows surface imaging using a pattern that has multiple lines of light. Incremental shifting of the line pattern and other techniques help to compensate for inaccuracies and confusion that can result from abrupt transitions along the surface, whereby it can be difficult to positively identify the segments that correspond to each projected line. In FIG. 3, for example, it can be difficult, over portions of the surface, to determine whether line segment 17 originates from the same line of illumination as line segment 18 or adjacent line segment 19.

An exemplary embodiment of the present disclosure addresses the need for accurate contour imaging of teeth and other intraoral features by providing a triangulation-based 3-D imaging apparatus that rapidly scans a line of light onto a subject surface at successive spatial increments using a highly compact and efficient arrangement of components. Unlike previously disclosed illumination solutions, the apparatus described herein performs the scan function automatically once it has been properly positioned within the mouth and enabled. The apparatus employs illumination from a laser source, optics to generate line images, and a transport mechanism that is designed to systematically scan tooth surfaces without requiring practitioner intervention in many cases. Because the device seats securely within the mouth of the patient, movement is constrained, eliminating the complex task of stitching together successive images in order to generate a full scan of the dental arch.

Figure 4B:
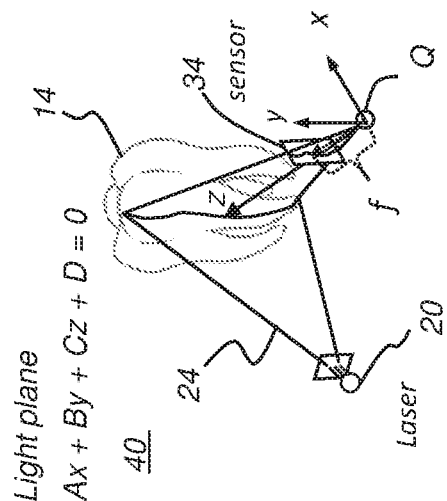
FIGS. 4A and 4B are schematic diagrams that show aspects of operation for a scanning apparatus of the present disclosure.
Figure 4A:
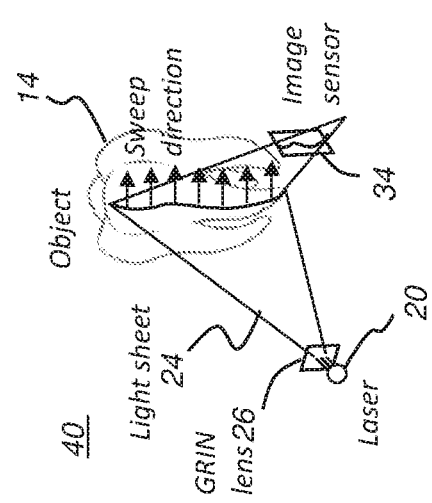

The schematic diagrams of FIGS. 4A and 4B show aspects of operation for a scanning apparatus 40 of the present disclosure. A laser 20 or other suitable light source directs a light sheet 24, formed by a lens 26 such as a gradient index lens (GRIN), towards tooth 14 or other intraoral feature. Light sheet 24 forms a line of light on the tooth surface; distortion of the projected line is detected by camera or image sensor 34 having appropriate image forming optics and is used to characterize the surface one line at a time. The focal distance f of image sensor 34 optics is shown, along with reference x, y, z axes. Light from laser 20 can be directed to optic 26 through a fiber optic light guide (not shown). Additional scanning apparatus components such as a rotating reflective surface, not shown in FIGS. 4A and 4B, sweep the generated light sheet 24 across the surface of tooth 14. In the context of the present disclosure, the term "scanning" can encompass both the sequenced, scanned projection of light features onto the object tooth or other surface and the simultaneous capture of scanned image content during light feature projection.

The coordinate position of light sheet 24 can be expressed using the equation:

$$Ax+By+cZ+D=0,$$

wherein A, B, C, and D are plane parameters in 3D space or real-world coordinates (x, y, z) with the origin Q indicated in FIG. 4B. In FIG. 4B, real-world coordinates coincide with camera 34 coordinates. Rays emitted from the origin Q pass through points of the distorted line on the tooth 14 surface. The ray vector, assumed to start from the coordinate origin (0, 0, 0), is determined by the camera 34 calibration matrix and image point location on the sensor array within the camera. The intersection of the ray vector with light sheet plane 24 gives the 3D coordinates of the object reflectance site.

Laser projection can use a laser diode or fiber laser distal with respect to the laser and a GRIN lens 26 for miniaturized optical layout. The camera 34, also referred to herein as image sensor 34, has a short distance of total track length to fit into a small operating space.

In operation, each image capture obtains the surface profile along a single projected line. Sweeping the scan unit across the tooth 14 or other object obtains successive surface profiles along adjacent lines, showing the 3D shape of the object.

In addition to surface contour characterization, the scanning apparatus of the present disclosure can also be utilized to acquire color texture information from the scanned surface. Laser 20 can be a white light laser, with polychromatic color content for providing color images. Alternately, individual single-color lasers, such as one each of red, green, and blue lasers, can be used for scanning. Multiple laser sources can share the same light path, combined using dichroic combiners, for example, using techniques well known to those skilled in the color imaging arts. Or, red, green, and blue light from individual single-color lasers can be coupled into the same fiber optic light guide to be conveyed to optic 26. Captured line images of a single color, such as images showing only projected lines of blue light, can be used for surface contour characterization as well.

The sensor array can be a full color sensing array or can be a monochrome light sensing array, with its sensing output timing synchronized with excitation timing of individual single color laser sources in order to obtain component color content for projected line features.

Figure 5B:
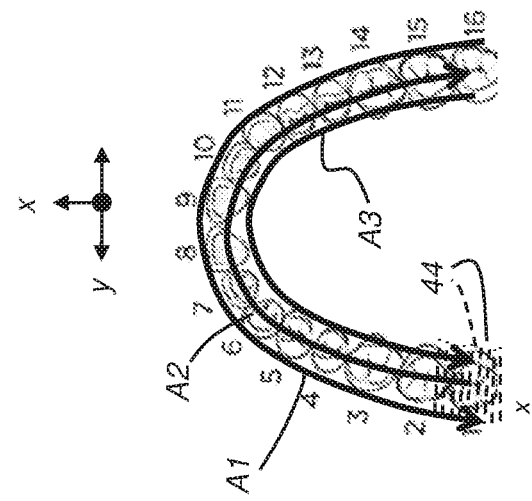
FIGS. 5A and 5B are top view schematic diagrams that show scan paths for the transport apparatus of the present disclosure.
Figure 5A:
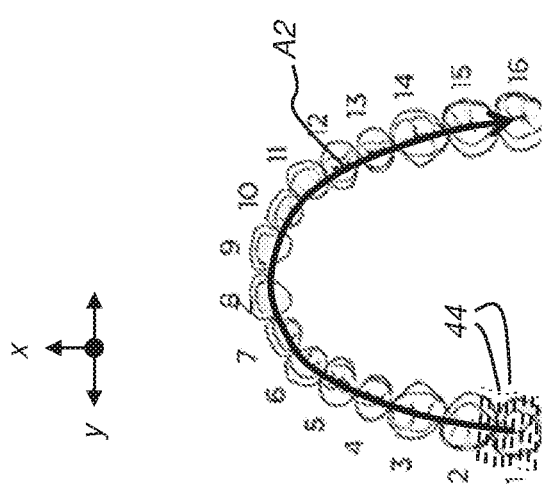

The schematic top view diagram of FIGS. 5A and 5B give two examples of a sweep scheme for scan positions 44 along the tooth arch for teeth numbered 1-16. For this scan sequence, scanning apparatus 40 is translated along a curved or arcuate track A2 that approximates the overall curvature of the dental arch. A representative number of scan positions 44 are shown. In practice, individual scan positions 44 would be tightly spaced and would cover all of the arch, or some designated portion of the dental arch that is of interest.

In FIG. 5B, three piecewise-parallel tracks A1, A2, and A3 are shown. The sweeping of the scan unit can use a micro-mechanical translation apparatus urged along the respective tracks A1, A2, A3 along the dental arch, as described in more detail subsequently.

For FIGS. 5A and 5B, axis y is the local light sheet orientation. x is the local translation orientation at the start of the scan sequence shown, beginning at the bottom left and moving upward in the orientation of FIGS. 5A, 5B. The scanning apparatus 40 translates over one or more of tracks A1, A2, A3 along the arch, such as with the aid of a micro-mechanical carrier. FIG. 5A shows the occlusal scan along the track A2. Track A1 is suitable for the buccal scan; track A3 is suitable for the lingual scan. For the average adult patient, the full arch scan length is around 16 cm. At each scan position 44, the light sheet width on the tooth can be about 10 mm or more. Full scans along each of tracks A1, A2, A3 could cover the whole tooth area for the dental arch.

Figure 6:
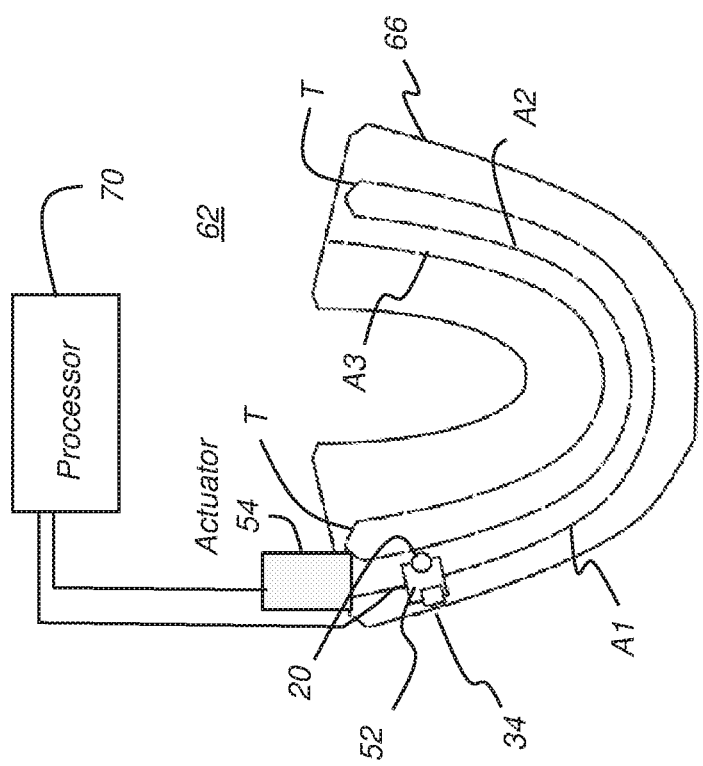
FIG. 6 is a top view schematic that shows an arrangement of a bite portion of an intraoral fixture.

The schematic diagram of FIG. 6 shows components of the imaging apparatus for providing the scan sequence of FIGS. 5A and 5B. In a bite portion 66 of an intraoral imaging fixture 62, a transport apparatus 52, driven by an actuator 54, conveys a camera or other image sensor 34 along one or more tracks, shown as A1, A2, and A3. A laser 20 or other suitable light source is directed to the patient's dentition from transport apparatus 52. Laser 20 may be stationary on transport apparatus 52 or remotely located and coupled to a fiber optic for conveying the light energy to transport apparatus 52. Actuator 54 can be a stepper motor or other device and may be mounted in stationary position, as shown in FIG. 6, or can alternately be mounted to transport apparatus 52. A variety of mechanical couplings can be provided for moving transport apparatus 52 along the arcuate tracks A1, A2, A3. Control of actuator 54 and acquisition of image data from image sensor 34 can be provided by a control logic processor 70, which may be a dedicated microprocessor device or may be provided by software running on a computer or other apparatus. Processor 70 is in signal communication with display and storage components of the imaging apparatus, as described in more detail subsequently.

Transport apparatus 52 can be configured for transit over a single track in a single direction. However, improved coverage of the tooth surface is available when using multiple tracks, or with some alternate arrangement that positions camera or other image sensor 34 at different angles. In the exemplary embodiment shown in FIG. 6, transport apparatus 52 travels down each of three tracks A1, A2, and A3, switching from one track to the next at a transition T. Each track offers imaging of the tooth surface from a different perspective, allowing improved coverage of buccal, lingual, and occlusal surfaces.

Because intraoral imaging fixture 62 is held in position within the patient's mouth, additional advantages are provided over hand-held scanner arrangements. The imaging apparatus can selectively position transport apparatus 52 so that it is opposite particular teeth. Thus, imaging of only a portion of the mouth is possible, such as imaging a single tooth for example, or imaging the occlusal surface of one or two teeth.

Figure 7:
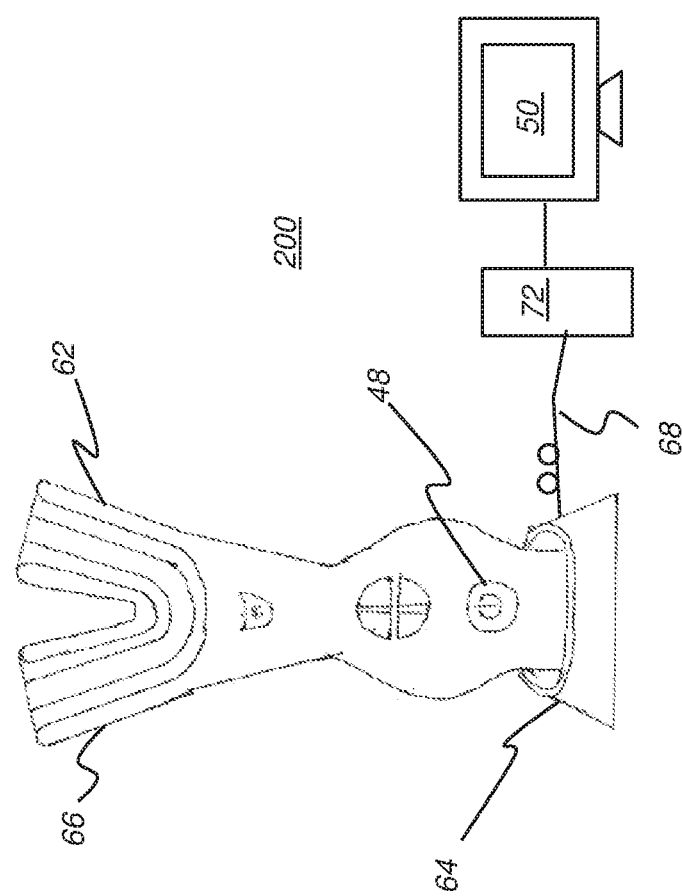
FIG. 7 is a diagram showing an imaging apparatus that uses an intraoral fixture.

The schematic diagram of FIG. 7 shows an imaging apparatus 200 with intraoral fixture 62 seated within a holder 64, such as a charging device or other apparatus for storing fixture 62 when not in use. A control such as an operator control switch 48 can be provided for initiation or pausing of the scan sequence, as described in more detail subsequently. In the exemplary embodiment shown in FIG. 7, imaging apparatus 200 has a computer 72 that is in signal communication with fixture 62, such as over a cable 68 or wireless connection. Computer 72 and display 50 can provide an operator interface that allows precise control of imaging behavior, as described in more detail subsequently.

Fixture 62 allows imaging of the full dental arch of the patient, or some portion of the dental arch, as needed, depending on the configuration. To scan the full mouth, the patient can insert bite portion 66 to scan the lower teeth first, then reverse the vertical orientation of fixture 62 in order to scan the upper teeth. Alternately, the upper arch can be scanned first, followed by the lower arch. In addition, the device can be controlled, using commands from a processor or computer, to scan only a portion or selected portions of the full dental arch as required by the practitioner.

Figure 8:
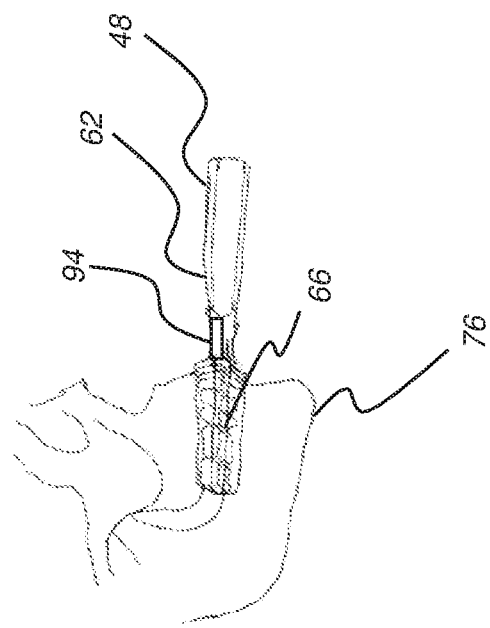
FIG. 8 is a side view schematic that shows a bite portion in place in the patient's mouth.

Referring to the schematic side view diagram of FIG. 8, there is shown intraoral fixture 62 as it is positioned for scanning teeth within the mouth of a patient 76, according to an embodiment of the present disclosure. Patient 76 holds fixture 62 by biting down on the device, gripping fixture 62 in place, clamped within the jaws during the scan. Control switch 48 allows the patient to initiate the scan sequence for self-scanning, without the assistance of a technician or practitioner. An optional preview camera 94 can be mounted within fixture 62 for providing a preview image that shows at least some portion of the scan area. According to an embodiment of the present disclosure, preview camera 94 displays a reflective image that is indicative of fixture 62 position on display 50 (FIG. 7). The image can be in two or more colors (polychromatic) or monochrome, for example. This display allows the viewer or other technician or practitioner to determine whether or not further adjustment or re-positioning of the fixture 62 would be useful for subsequent scanning. This feature can be of particular utility where it is useful to place fixture 62 for scanning a partial subset of the dental arch, such as where one or more teeth are to be scanned. Additionally, color images captured by preview camera 94 can provide color texture corresponding to the final surface contour.

According to an exemplary embodiment of the present disclosure, the fixture 62 has a scanning orientation, so that the scanning apparatus can be positioned to face either the upper or the lower dental arch. This configuration enables fixture 62 to be reversed for separately scanning each half of the patient's dentition.

Figure 9B:
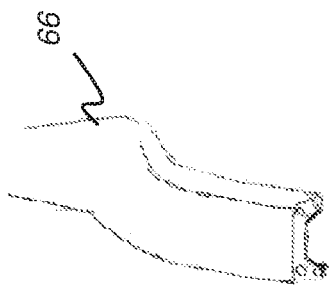
FIGS. 9A and 9B show two alternate arrangements for bite portions.
Figure 9A:
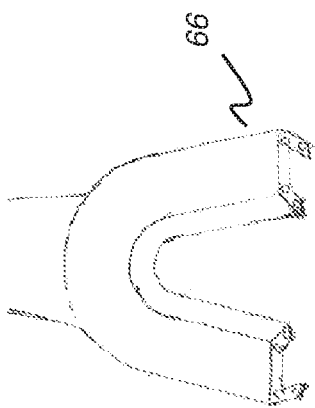

FIGS. 9A and 9B show two alternate arrangements for bite portions 66. In FIG. 9A, bite portion 66 is configured to cover the full arch of the patient, allowing a full scan of half of the patient's mouth at a time, before repositioning to scan the other half. FIG. 9B shows an arrangement for scanning only a portion of an arch.

It should be noted that different sizes of fixture 62 can be used for patients of different mouth sizes, allowing a suitable scan arrangement for patients having different builds. Alternately, an adjustable fixture can be provided, using a hinged arrangement, for example to suit the fixture to the arch shape of a particular patient.

Figure 10B:
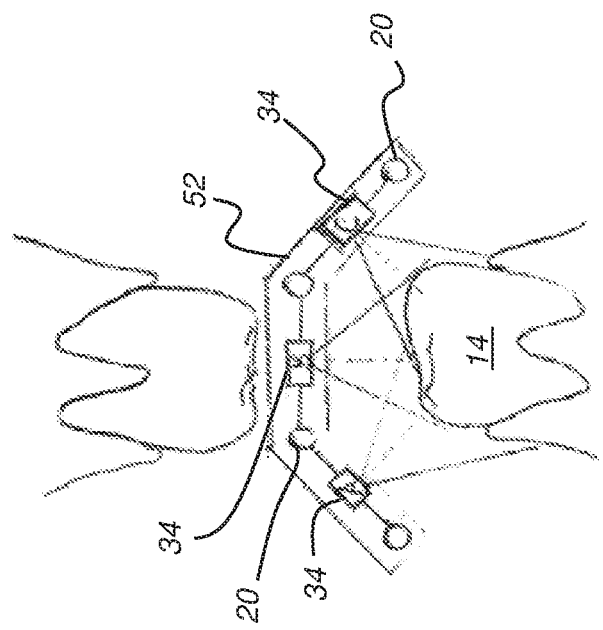
FIGS. 10A, 10B, 10C, and 10D show different arrangements of a transport apparatus within the bite element.
Figure 10A:
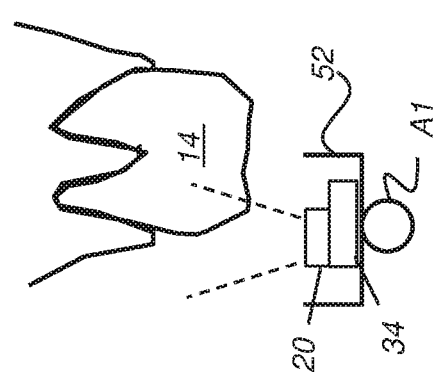
Figure 10C:
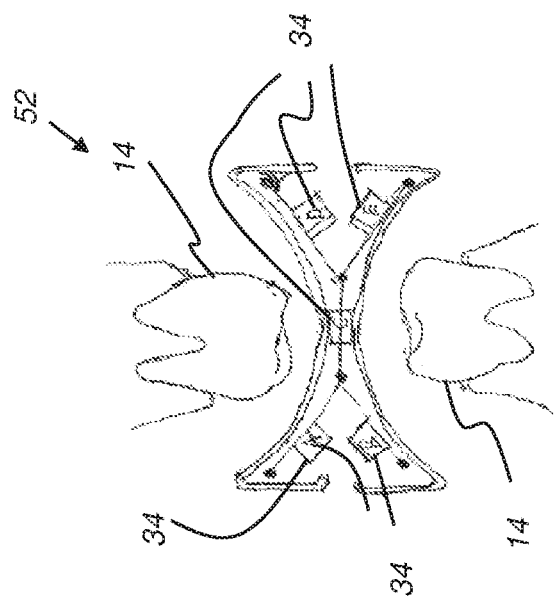

FIGS. 10A, 10B, and 10C show different arrangements of transport apparatus 52 within bite portion 66. The cross sectional view of FIG. 10A shows transport apparatus 52 moving along track A1 to scan one side of teeth 14 in the dental arch. Transport apparatus 52 would be suitably shifted in position, horizontally from the view of FIG. 10A, in order to scan other surfaces.

FIG. 10B shows a cross-sectional embodiment in which transport apparatus 52 has three paired imaging systems, each with a camera 34 and a laser 20 source. This arrangement allows a single scan to acquire surface data from all exposed portions of the teeth 14 in an arch.

Figure 10D:
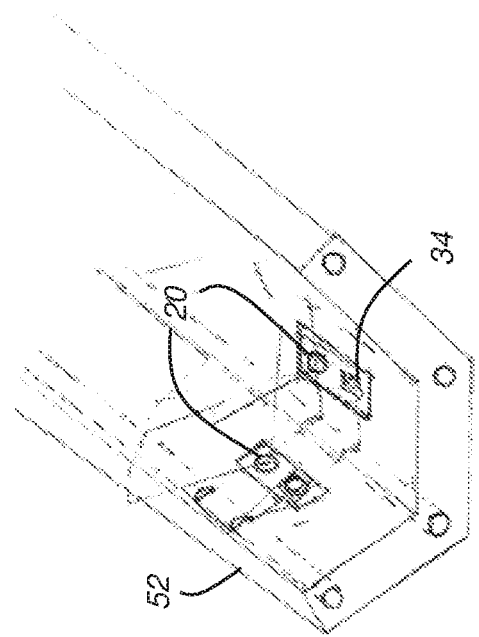

FIG. 10C shows an arrangement of transport apparatus 52 having two cameras 34 and two lasers 20, for scanning opposite tooth surfaces in a single scan traversal along the track. FIG. 10D shows an alternate arrangement that allows scanning of both upper and lower arch surfaces in a single traversal of transport apparatus 52.

Additional features of exemplary fixture 62 can be used to more easily position the fixture 62 relative to a patient's teeth or arch. Control software can be programmed to restrict the scan to a limited portion of the non-linear, curved or arcuate scan path. In some exemplary embodiments, fixture 62 can be removably fixed to the patient's upper or lower jaw for depth resolved image scanning so that the patient need not bite down on the fixture 62 during a scan. In one exemplary embodiment, a fixture 62 can be held in place by tension or elasticity characteristics that push against multiple (e.g., opposing) sides of the inside or the outside of the upper or lower jaw.

One or more laser diodes can be used for generating light, with supporting optics and with a reflective micro-electromechanical systems (MEMS) device for forming and scanning the patterned light over the tooth surface. The high speeds available from the light scanning apparatus allow this solution to be used with video 3D capture devices and other high speed image sensing components. Alternately, other light sources, such as light-emitting diodes (LEDs) could be used.

Any of a number of types of conventional drives such as motors, electromechanical mechanisms or other devices can be used as actuator 54 that is mechanically coupled to transport apparatus 52 for providing the prescribed translation (e.g., linear or non-linear) along track A1, A2, A3. According to an embodiment of the present disclosure, actuator 54 can be a motor that urges scanner(s) along the track using a cord, cable, or string. A pulley mechanism can be provided for providing this C-scan or x-axis motion of scanner(s) along the curved or arcuate track.

Figure 11:
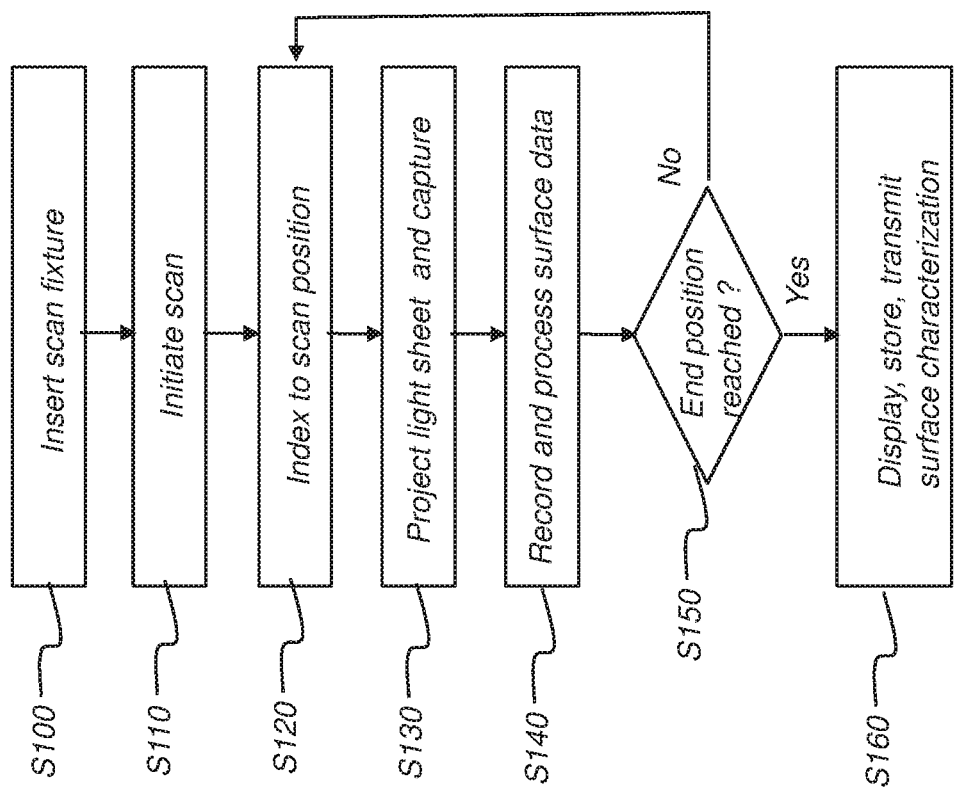
FIG. 11 is a logic flow diagram showing scan steps for intraoral imaging.

FIG. 11 is a logic flow diagram showing scan steps for intraoral imaging. In a preparation step S100, the scan fixture is positioned in the patient's mouth for scanning the patient's dentition. Preparation step S100 can also entail programming the fixture 62 to scan only a specific portion of an arch, such as only one, two, or three teeth, for example, as described in more detail subsequently. In a scan initiation step S110, the patient or practitioner initiates scanning. Initiation can be performed using control switch 48, as described previously, or using some other input device or control command. In an indexing step S120, the transport apparatus of fixture 62 moves to its start position for scanning. Step S120 begins a repeat loop, projecting the light sheet and capturing the resulting image in an acquisition step S130 and recording and processing the surface data in a surface data processing step S140. A looping step S150 determines whether or not the end position of the scan has been reached. If not, the transport apparatus is incrementally indexed to the next scan position and steps S120, S130, and S140 are repeated. Once the end position has been reached, scanning and processing terminate and a display step S160 provides display data for the surface characterization that has been computed. This data can also be stored in a memory or other storage unit and transmitted to another processor as needed.

Figure 12:
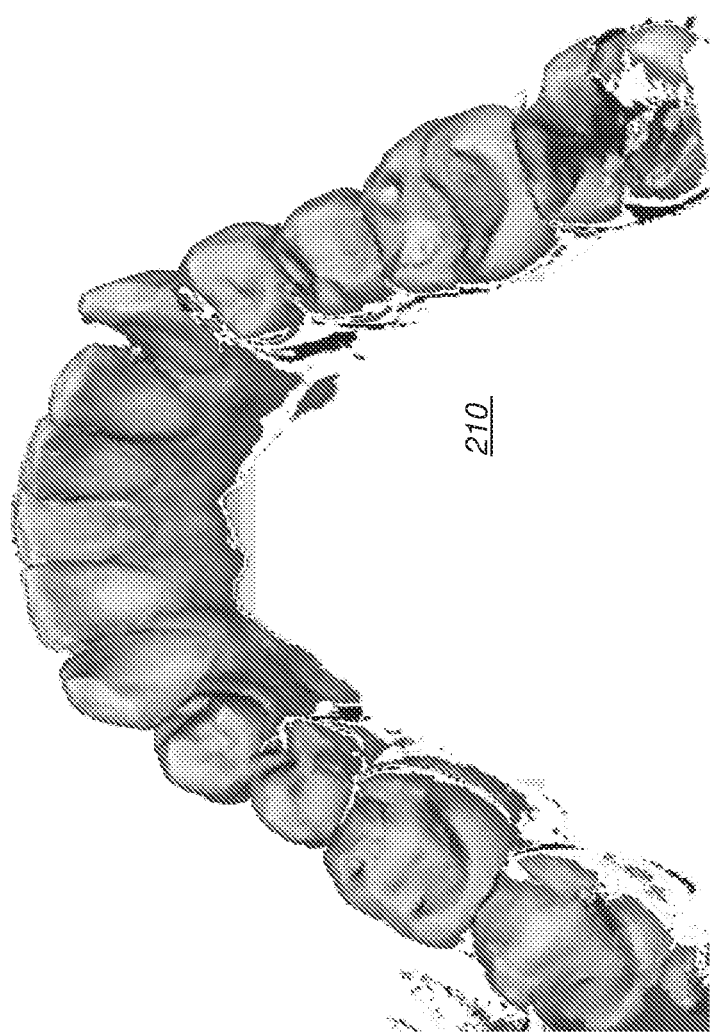
FIG. 12 shows an exemplary point cloud image.

FIG. 12 shows an exemplary 3D surface contour image 210 that can be obtained in accordance with certain exemplary method and/or apparatus embodiments of the application.

Operator Interface

Figure 13:
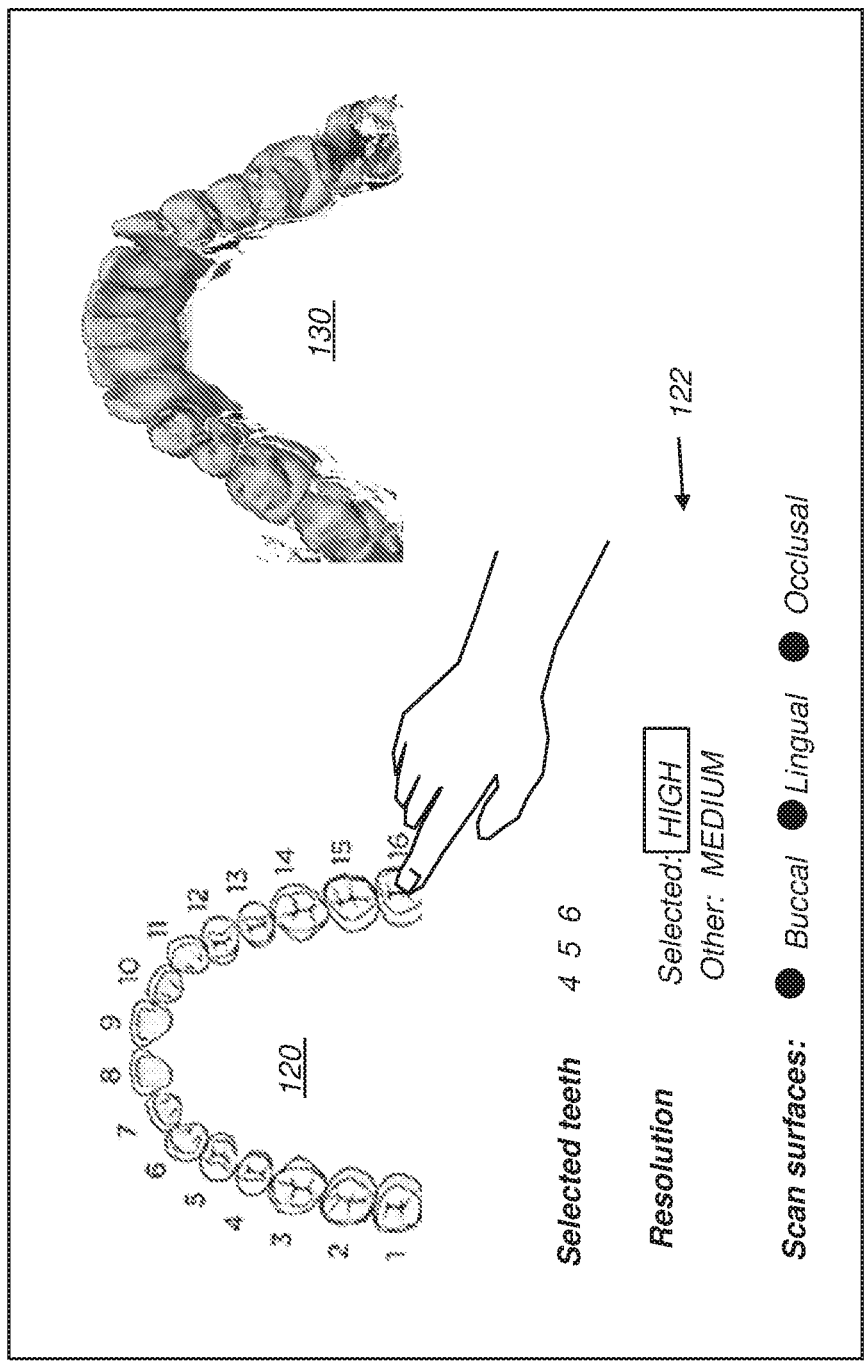
FIG. 13 shows an exemplary operator interface for controlling the scan pattern according to an embodiment of the present disclosure.

FIG. 13 shows an exemplary operator interface for controlling operation of the imaging apparatus and controlling the scan pattern within fixture 62 according to an embodiment of the present disclosure. A touch screen version is shown. A graphic template 120 enables the operator or practitioner to specify the dental arch for scanning and to identify a region of interest of the arch. A display portion 130 displays the point cloud that is generated. According to an embodiment, selection buttons 122 are provided that allow control of various parameters such as resolution for particular teeth, scan surfaces for the arch or arch portion, and other parameters.

According to an embodiment of the present disclosure, a lower resolution scan can be provided for some portions of the dental arch, with higher resolution over an identified region of interest. This feature can reduce overall scan time and enable a full scan with detailed information where needed.

Consistent with an embodiment of the present invention, a computer program can use stored instructions that perform on image data that is accessed from an electronic memory. As can be appreciated by those skilled in the image processing arts, a computer program for operating the imaging system and probe and acquiring image data in exemplary embodiments of the application can be utilized by a suitable, general-purpose computer system operating as processor as described herein, such as a personal computer or workstation. However, many other types of computer systems can be used to execute the computer program of the present invention, including an arrangement of networked processors, for example. The computer program for performing exemplary method embodiments may be stored in a computer readable storage medium. This medium may include, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing exemplary method embodiments may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the application, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the application. Memory is also used as the data workspace for executing and storing intermediate and final results of calculations and other processing. Computer-accessible memory can be volatile, non-volatile, or a hybrid combination of volatile and non-volatile types.

It will be understood that computer program products of the application may make use of various image manipulation algorithms and processes that are well known. It will be further understood that computer program product exemplary embodiments of the application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product exemplary embodiments of the application, are not specifically shown or described herein and may be selected from such algorithms, systems, hardware, components and elements known in the art.

Certain exemplary method and/or apparatus embodiments of the application can provide a scanner to characterize surfaces of teeth, gum tissue, and other intraoral features. Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by at least the following claims.

The invention claimed is:

1. An intraoral scanning apparatus comprising:
 a) a mouthpiece;
 b) a transport apparatus that defines at least a first curved track and a second curved track within the mouthpiece, wherein the first curved track is connected to the second curved track at a transition;
 c) an image sensor movable along the first curved track and the second curved track, wherein the image sensor is configured for moving between the first curved track and the second curved track at the transition;
 d) a scanner movable along the first curved track and the second curved track, wherein the scanner is configured for moving between the first curved track and the second curved track at the transition, and wherein the scanner is configured for scanning in synchronization with the image sensor and having an illumination source that has:
   (i) a laser light source;
   (ii) beam-shaping optics in the path of the laser light source for forming a linear light pattern;
 e) at least one actuator energizable to move the image sensor and scanner along the first curved track for image acquisition of an intraoral surface at a first perspective and energizable to move the image sensor and scanner along the second curved track for image acquisition of the intraoral surface at a second perspective;
 f) a control logic processor that synchronizes the scanner and image sensor for automated acquisition of surface contour data; and
 g) a display in signal communication with the control logic processor to process and display the acquired surface contour data.

2. The scanning apparatus of claim 1 wherein the acquired surface contour data includes images of the linear light pattern sequentially projected onto intraoral features.

3. The scanning apparatus of claim 1 further comprising an operator interface in signal communication with the control logic processor and configured to accept operator instructions that control scanner resolution.

4. The scanning apparatus of claim 1 further comprising an operator interface in signal communication with the control logic processor and configured to accept operator instructions that control a start and a stop position for acquiring surface contour data from the scanner.

5. The scanning apparatus of claim 1 further comprising an operator interface that allows control of resolution of the acquired surface contour image.

6. The scanning apparatus of claim 1 wherein the scanner further comprises a micro-electromechanical systems device.

7. The scanning apparatus of claim 1 wherein the at least one actuator moves along the first curved track and the second curved track with the transport apparatus.

8. The scanning apparatus of claim 1 wherein the at least one actuator has a stationary position within the mouthpiece.

9. The scanning apparatus of claim 1 wherein the at least one actuator travels with the transport apparatus.

10. The scanning apparatus of claim 1 wherein the scanner and image sensor are movable in a direction orthogonal to the first curved track and the second curved track.

11. The scanning apparatus of claim 1 wherein the laser light source has a fiber optic light guide conveying light from a remotely located laser.

12. The scanning apparatus of claim 1 wherein the laser light source conveys polychromatic light to the intraoral surface.

13. The scanning apparatus of claim 1 wherein the laser light source conveys monochromatic light to the intraoral surface.

14. The scanning apparatus of claim 1 further comprising a preview camera that is configured to acquire color texture data corresponding to the acquired surface contour data.

15. A method for intraoral scanning comprising:
 a) providing a mouthpiece having a scanner apparatus with a camera, wherein the scanner apparatus is movable along a first curved track and a second curved track within the mouthpiece and scans a line of light onto a subject surface that is within the camera FOV, and wherein the scanner apparatus is configured for moving between the first curved track and the second curved track at a transition;
 b) urging the scanner apparatus in a forward direction along the first curved track to a first position;
 c) scanning the subject surface while urging the scanner apparatus forward from the first position along the first curved track to a second position;
 d) moving the scanner apparatus from the first curved track to the second curved track at the transition; and
 e) urging the scanner apparatus along the second curved track in a backward direction with respect to the first curved track and at least to the first position.

16. The method of claim 15 further comprising pulsing the line of light at a first rate synchronous with image capture by the camera.

17. The method of claim 16 further comprising pulsing the line of light at a second rate between a third position and a fourth position that are both outside of a track portion between the first and second positions.

18. The method of claim 16 wherein the first rate is variable according to an entered instruction.

19. The method of claim 15 wherein a section of the first curved track from the first to the second position spans only a partial portion of teeth along a dental arch.

20. The method of claim 15 further comprising changing the urging speed according to a scan resolution.

21. The method of claim 15 wherein the first and second positions span a full dental arch.

22. A method for intraoral scanning comprising:
 a) in response to an operator instruction, indexing a scanner apparatus in a first direction to a first position along a first curved track along an intraoral mouthpiece;
 b) scanning at least a first tooth between the first position and a second position along the first curved track;
 c) moving the scanner apparatus from the first curved track to a second curved track;
 d) moving the scanner apparatus along the second curved track and scanning at least the first tooth by indexing the scanner apparatus in a second direction opposite the first direction;
 e) processing scanning results to generate surface contour for at least the first tooth; and
 f) displaying the surface contour for at least the first tooth.

23. The method of claim 22 wherein the scanning operation is continuous during indexing.

* * * * *